United States Patent
Koulik et al.

(10) Patent No.: US 6,258,371 B1
(45) Date of Patent: Jul. 10, 2001

(54) METHOD FOR MAKING BIOCOMPATIBLE MEDICAL ARTICLE

(75) Inventors: Edouard Koulik, Maastricht; Larik Vincent, Landgraaf; Patrick Cahalan, Geleen, all of (NL); Eric Fogt, Maple Grove, MN (US); Kazuhiko Ishihara, Tokyo; Nobuo Nakabayashi, Chiba-Ken, both of (JP)

(73) Assignee: Medtronic Inc, Minneapolis, MN (US)

( * ) Notice: Subject to any disclaimer, the term of this patent is extended or adjusted under 35 U.S.C. 154(b) by 0 days.

(21) Appl. No.: 09/054,389

(22) Filed: Apr. 3, 1998

(51) Int. Cl.$^7$ ............................. A61F 13/00; A61F 2/00
(52) U.S. Cl. ..................................... 424/422; 424/423
(58) Field of Search ............................. 424/422, 423

(56) References Cited

U.S. PATENT DOCUMENTS

| | | | |
|---|---|---|---|
| 4,733,665 | 3/1988 | Palmaz | 128/343 |
| 4,800,882 | 1/1989 | Gianturco | 128/343 |
| 4,886,062 | 12/1989 | Wiktor | 128/343 |
| 5,368,733 | 11/1994 | Nakabayashi | 210/500.23 |
| 5,372,600 | 12/1994 | Beyar et al. | 606/108 |
| 5,453,467 | 9/1995 | Bamford et al. | 525/287 |
| 5,466,853 | 11/1995 | Koinuma et al. | 558/169 |
| 5,658,561 | 8/1997 | Nakabayashi et al. | 424/78.37 |
| 5,679,569 * | 10/1997 | Verhoeven et al. | 514/56 |
| 5,679,659 | 10/1997 | Verhoeven et al. | 514/56 |
| 5,866,113 * | 2/1999 | Hendriks et al. | 424/78.17 |

FOREIGN PATENT DOCUMENTS

| | | |
|---|---|---|
| 580435 | 1/1994 | (EP) . |
| 54-063025 | 5/1979 | (JP) . |
| 3039309 | 2/1991 | (JP) . |
| WO 9316117 | 8/1993 | (JP) . |
| 407238124 * | 9/1995 | (JP) . |
| 9003132 | 1/1997 | (JP) . |
| WO 9315775 | 8/1993 | (WO) . |

* cited by examiner

Primary Examiner—Thurman K. Page
Assistant Examiner—Todd D Ware
(74) Attorney, Agent, or Firm—Thomas F. Woods; Michael J. Jaro; Harold Patton

(57) ABSTRACT

A method for making a biocompatible medical article, and preferably, a blood compatible medical article, through the use of a copolymer coating. The copolymer coating is synthesized using methacrylate or acrylate monomers with a functional group (primary amino group) for subsequent attachment of heparin. Synthesis of the copolymer coating is carried out using the proper proportion of hydrophobic monomer/hydrophilic monomer/functional monomer in order to optimize the solubility of the copolymer in alcohol, its insolubility in water (before and after heparin coupling), the heparin coupling efficacy and heparin bioactivity. Once the copolymer coating is fashioned, a medical article is coated with it. The coating is thereafter dried and heparin attached. In such a manner the present invention provides for a method for making a biocompatible medical article, and preferably, a blood compatible medical article.

11 Claims, 7 Drawing Sheets

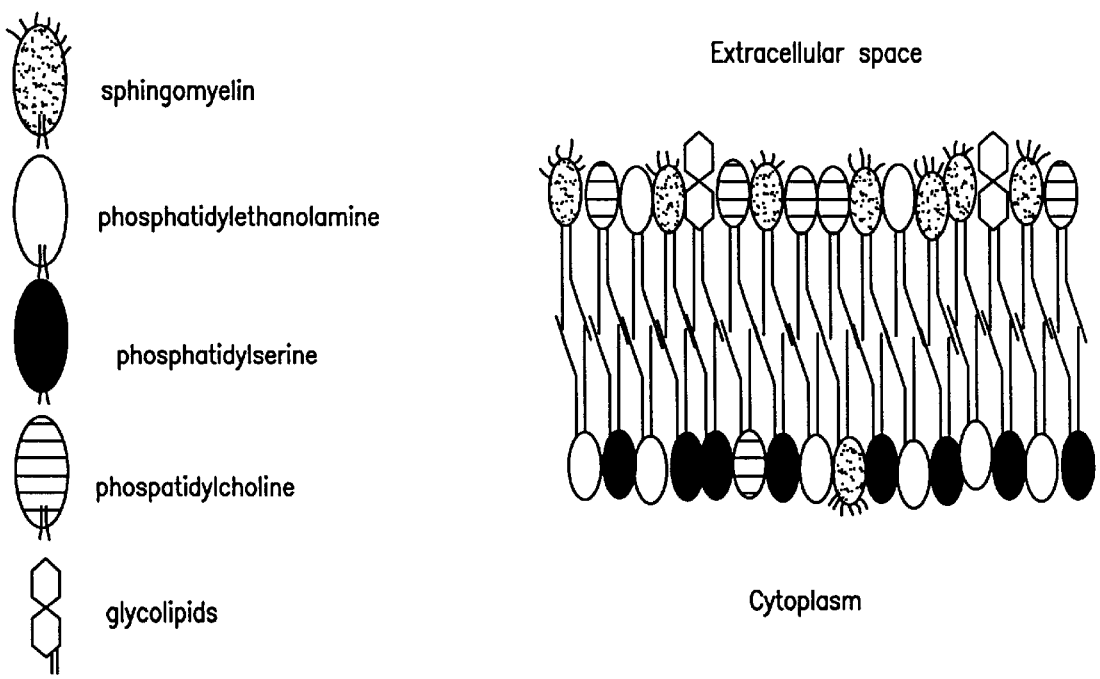
FIG. IA

METHOD FOR MAKING BIOCOMPATIBLE MEDICAL ARTICLE

FIELD OF THE INVENTION

This invention relates to a method for making a biocompatible medical article, and preferably, a blood compatible medical article. In particular, this invention relates to a method of making blood compatible medical articles through the use of an alcohol-based polymer carrier suitable for the subsequent attachment of a bioactive molecule, such as heparin.

BACKGROUND OF THE INVENTION

The development of medical articles that contact physiological fluids, particularly blood, is a rapidly developing area of medicine. This has been hampered, however, by the lack of suitable synthetic materials that are stable when contacted with such fluids.

Adverse reactions between materials and blood components are predominant factors limiting the use of synthetic materials that come into contact with physiological fluids. For example, catheters, vascular grafts, and the like, tend to serve as a nidus, or focus, for the formation of thrombi (blood clots). Initial contact of such materials with blood results in deposition of plasma proteins, such as albumin, fibrinogen, immunoglobulin, coagulation factors, and complement components. The adsorption of fibrinogen onto the surface of the material causes platelet adhesion, activation, and aggregation. Other cell adhesive proteins, such as fibronectin, vitronectin, and von Willebrand factor (vWF) also promote platelet adhesion. As a result, the continual use of anticoagulants in conjunction with the introduction of such materials to the body is often necessary.

Furthermore, complement activation occurs when materials are introduced into blood. Adsorption of large amounts of IgG, IgM, and C3b onto surfaces causes activation. Subsequently, complexes may be formed which contribute to undesirable immune responses, such as proteolysis, cell lysis, opsonization, anaphylaxis, and chemotaxis. As a result, these responses render such materials incompatible with the living body.

A number of approaches have been suggested to improve the biocompatibility, and even blood compatibility, of medical articles. One approach which has met with some success is to couple anticoagulants to the surface of biologically inert materials to impart antithrombogenic characteristics to the materials. Among the anticoagulants bound to the surface is heparin. It has been found generally that heparinized surfaces greatly reduce the generation of thrombus and thus cellular activation of blood contacting them, because heparin is a potent inhibitor of thrombin generation.

Although many different methods have been disclosed for heparinizing a surface, the problem still exists to combine in one method the following features: (I) technological simplicity and wide applicability in terms of the substrate materials; (II) stability/durability of coating, (III) high bioactivity of attached heparin. (I) The most simple and universal method of surface modification of a medical article is a dip coating (or pumping through) the device in a solution of the proper polymer, followed by the solvent evaporation. Since the organic solution should be preferably used for the good wetting and coating of plastics, the haemocompatible polymer must be soluble in a non-toxic, chemically not aggressive organic solvent, such as, for example, ethanol. (II) Such a polymer, however, has to be insoluble in water, because the coating should be stable upon the contact with blood. (III) The polymer must include heparin in its structure or must have the functional chemical group, which is required for subsequent heparin coupling. Preferably, the polymer must be a copolymer, having both hydrophobic and hydrophilic segments. The hydrophobic segments are required to anchor the polymer to the substrate surface, while hydrophilic segments must provide an extra mobility to heparin molecule, which is important to achieve a high biological activity of heparin.

It is thus an object of the present invention to provide a method of producing a haemocompatible coating from a polymer or copolymer as the primary layer which is soluble in a non-toxic, chemically not aggressive organic solvent, such as, for example, ethanol.

It is a further object of the present invention to provide a method of producing such a polymer or copolymer which is also insoluble in water and will thus be stable upon the contact with blood.

It is a further object of the present invention to provide a method of producing such a polymer or copolymer which has a functional chemical group, which is required for subsequent heparin coupling.

It is a further object of the present invention to provide a method of producing such a polymer or copolymer which has both hydrophobic and hydrophilic segments.

SUMMARY OF THE INVENTION

The present invention meets these and other objects by providing a method for making a biocompatible medical article, and preferably, a blood compatible medical article, through the use of a copolymer coating. The copolymer coating is synthesized using methacrylate or acrylate monomers with a functional group (primary amino group) for subsequent attachment of heparin. Synthesis of the copolymer coating is carried out using the proper proportion of hydrophobic monomer/hydrophilic monomer/functional monomer in order to optimize the solubility of the copolymer in alcohol, its insolubility in water (before and after heparin coupling), the heparin coupling efficacy and heparin bioactivity. Once the copolymer coating is fashioned, a medical article is coated with it. The coating is thereafter dried and heparin attached. In such a manner the present invention provides for a method for making a biocompatible medical article, and preferably, a blood compatible medical article.

BRIEF DESCRIPTION OF THE DRAWINGS

FIG. 1A illustrates the basis upon which the present invention of a copolymer coating synthesized using methacrylate or acrylate monomers with a functional group (primary amino group) for subsequent attachment of the biomolecule rests.

Figure 1B:
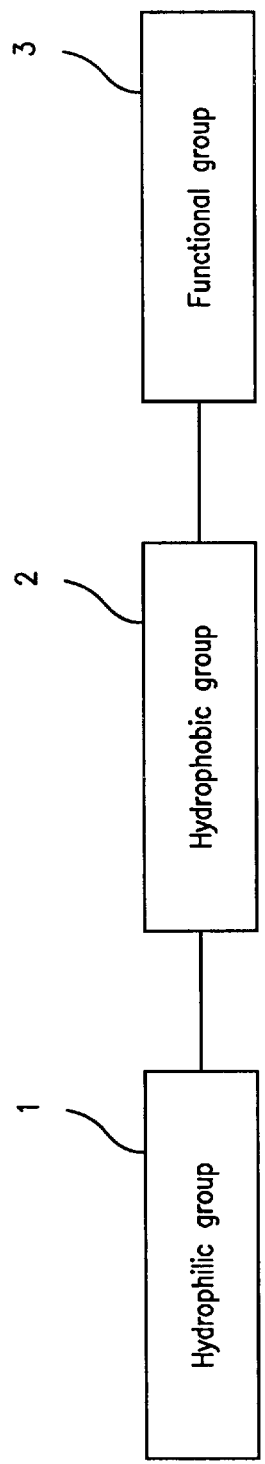
FIG. 1B depicts a block representation of a suitable copolymer coating used in the present invention.

The FIGS. are not necessarily to scale.

DETAILED DESCRIPTION OF THE DRAWINGS

As already discussed above, the biocompatibility of materials used in medical articles can be improved by attaching a biomolecule, preferably heparin, to the relevant surface(s) of the medical article. According to the present invention such a biomolecule may be attached through the use of a copolymer coating, the copolymer coating synthesized using methacrylate or acrylate monomers with a functional group (primary amino group) for subsequent attachment of the biomolecule. Using this method, the extent and severity of adverse reactions between the substrate and bodily fluids, particularly blood, is reduced.

Blood compatibility is much more complex than the compatibility of a material with other bodily fluids or tissues. This is because of the complex mixture of red cells, white cells, platelets, inorganic ions, and plasma proteins such as albumin, fibrinogens, and globulin in blood. Blood forms a clot or thrombus when injury occurs or when it is contacted by a foreign substance. Almost all materials set off this clot-forming process, and generally soon thereafter become coated with an irreversible clot of varying size. Such clots could have an adverse effect on the utility of such materials. Thus, particularly preferred materials of the present invention are particularly advantageous because they do not cause any significant coagulation or reaction of natural blood components as would occur in vivo, such as blood platelet activation and thrombin generation.

The materials of the present invention include a substrate and a biomolecule attached through the use of a copolymer coating, the copolymer coating synthesized using methacrylate or acrylate monomers with a functional group (primary amino group) for subsequent attachment of the biomolecule in an amount and orientation effective to provide an improved nonthrombogenic surface relative to the substrate without either the copolymer coating or the copolymer coating and the biomolecule. The contact between blood and a foreign surface initiates a complex process of thrombogenesis that involves platelet adherence, aggregation, and granular release; thrombin generation; and fibrin formation. As a consequence, there are a number of parameters that can be selected as a measure of a material's thrombogenicity. Thus, evaluation of the reactions at the blood-material interface therefore typically involves a multi-parameter (i.e., multi-assay) approach (e.g., platelet factor 4 (PF4) assay for platelet activation, thrombin-antithrombin (TAT) assay for thrombin generation, and clotting time test for general antithrombogenic properties) used herein can be sufficient to show the improvements resulting from the method of the present invention.

The blood compatibility of the material of the present invention can be demonstrated by reduced platelet activation and thrombin generation rate upon interaction with blood when compared to the material without the biomolecule attached through the copolymer coating synthesized using methacrylate or acrylate monomers with a functional group (primary amino group). By this it is meant that for a substrate to which there is a biomolecule, such as heparin, attached through copolymer coating synthesized using methacrylate or acrylate monomers, there is a reduction in the clotting time relative to the same substrate without the biomolecule and the copolymer coating synthesized using methacrylate or acrylate monomers with a functional group (primary amino group) for subsequent attachment of the biomolecule attached thereto when contacted with human blood according to the procedure outlined in the Examples. Preferably, the substrate surface of this invention is substantially nonthrombogenic, i.e., it has longer clotting time. Herein, a substantially nonthrombogenic substrate has clotting time at least 30% longer than conventional surface being tested at the conditions described elsewhere.

Platelet activation can also be determined by the release of Platelet Factor 4. For a substrate to which there is a biomolecule, such as heparin, attached through a copolymer coating synthesized using methacrylate or acrylate monomers, there is a reduction in the amount of Platelet Factor 4 released relative to the same substrate without the biomolecule attached through a copolymer coating synthesized using methacrylate or acrylate monomers when contacted with human blood according to the procedure outlined in the Examples. Preferably, this reduction is in an amount of at least about 20%, and more preferably, at least about 50%.

The blood compatibility of the material of the present invention can also be demonstrated by reduced thrombin-antithrombin (TAT) formation upon interaction with blood when compared to the material without the biomolecule attached through a copolymer coating synthesized using methacrylate or acrylate monomers. By this it is meant that for a substrate to which there is a biomolecule, such as heparin, attached through a copolymer coating synthesized using methacrylate or acrylate monomers with a functional group (primary amino group), there is a reduction in the number of thrombin-antithrombin (TAT) complexes formed relative to the same substrate without the biomolecule attached through a copolymer coating synthesized using methacrylate or acrylate monomers when contacted with human blood according to the procedure outlined in the Examples. Preferably, this reduction is in an amount of at least about 30%, and more preferably, at least about 50%.

The blood compatibility of the material of the present invention can be demonstrated by the increased clotting time upon interaction with blood when compared to the material without the biomolecule attached through a copolymer coating synthesized using methacrylate or acrylate monomers. By this it is meant that for a substrate to which there is a biomolecule, such as heparin, attached through a copolymer coating synthesized using methacrylate or acrylate monomers, there is a reduction in amount of elastase formed relative to the same substrate without the biomolecule and the copolymer coating synthesized using methacrylate or acrylate monomers with a functional group (primary amino group) for subsequent attachrment of the biomolecule thereto when contacted with human blood according to the procedure outlined in the Examples. Preferably, this increase in clotting time is in an amount of at least 50%, and more preferably, at least about 100%.

FIG. 1A illustrates the basis upon which the present invention of a copolymer coating synthesized using methacrylate or acrylate monomers with a functional group (primary amino group) for subsequent attachment of the biomolecule rests. As seen, the extracellular side of the membrane mostly consists of phosphoryl choline (PC) containing phospholipids such as phosphatidylcholine and sphingomielin. The phospholipids are assembled along the membrane in such a way that only polar PC groups are exposed to the extracellular space. Because the membrane of blood cells are not naturally thrombogenic, it is reasonable to conclude that a properly oriented PC group would be a biocompatible coating for medical articles.

Past attempts have been made to use phospholipid polar groups to obtain a biocompatible material. For example, 2-methacryloyloxyethyl phosphorylcholine (MPC) was offered in Japanese laid-open patent application 54-63025. This polymer has been suggested for use for the short term contact with blood, such as blood bags and the like. Nonetheless, polymers containing MPC have not, to date, proven wholly satisfactory for the long term contacting with blood or, further, in use with medical articles in contact with blood. In particular, several patents and patent application (e.g. the above-referenced Japanese application JPA-54-63,025 published May 21, 1979; U.S. Pat. Nos. 5,466,853; and 5,368,733) state MPC containing copolymers can be used on medical article as blood compatible coatings. Several recent studies on coating of oxygenators and stents with MPC copolymers did not lead to marketing of coated devices. The main drawback of MPC coating is that it is passive coating. Although it can reduce platelet adhesion, it does not reduce thrombin generation rate and it does not reduce platelet and leukocyte activation in blood measured by release of PF4 and elastase, respectively. It is a coupling of particular bioactive substances, e.g. heparin, that alters the properties of MPC copolymers rendering them with truly antithrombogenic properties. Nakabayashi U.S. Pat. No. 5,658,561 "Method Of Producing Anti-Thrombogenic Material And Material Produced Thereby" and assigned to Biocompatibles Limited, Uxbridge, England, for example, mentions the use of MPC and heparin, although the specific implementation of heparin grafting to MPC is not disclosed. Moreover, the method disclosed relates to the graft of such to regenerated cellulose, and requires a subbing layer, in the case of silicone medical articles, for example. There is, in fact, evidence that MPC copolymers do not influence the rate of thrombin generation and, in general, the rate of blood activation, presented in the tables below I and II. The present invention, in contrast, provides a coating which uses a MPC copolymers having heparin attached thereto so as to provide much improved biocompatibliity, reduce thrombin generation rate and platelet activation in blood measured by release of PF4, also seen in the tables I and II below.

FIG. 1B depicts a block representation of a suitable copolymer coating used in the present invention. As seen, the copolymer coating consists essentially of three groups, each group having a particular characteristic with regard to either water or the subsequent attachment of biomolecules. In particular, the copolymer coating has a first group 1 comprised of a hydrophilic moiety, a second group 2 comprised of a hydrophobic moiety and a third group 3 comprised of a functional moiety provided for the subsequent attachment of a biomolecule thereto.

The hydrophilic block 1 may be provided by the synthesis or polymerization of any number of possible suitable monomers or polymers including one or more monomers selected from the group consisting of acrylic or methacrylic monomers which have a hydrophilic moiety (which makes the monomer soluble in water and the copolymer formed therefrom wettable) including methacryloyl oxyethyl phosphorylcholine (MPC), acrylamide, poly(ethylene glycol) methacrylate, hydroxyethyl methacrylate, hydroxypropyl methacrylate, acrylic acid, methacrylic acid, 2,3-dihydroxypropyl acrylate, 2,3-dihydroxypropyl methacrylate, 3-sulfopropyl methacrylate, methacrylamidopropyltrimethylammonium chloride, or any of the homologues thereof. In the preferred embodiment the hydrophilic group is provided using methacryloyl oxyethyl phosphorylcholine (MPC).

The hydrophobic block 2 may be provided by the synthesis or polymerization of using any monomers which are not soluble in water, monomers or polymers including one or more monomers selected from the group consisting of butyl methacrylate, butyl acrylate, dodecyl methacrylate, dodecyl acrylate, heptyl acrylate, hexadecyl methacrylate, octyl methacrylate or any of the homologues thereof. In the preferred embodiment the hydrophobic monomer is provided using butyl methacrylate.

The functional group 3 may be provided by the synthesis or polymerization of any suitable monomers selected to provide the functional group for the subsequent attachment of a biomolecule, the functional group further being provided to synthesize and thus form the copolymers with the hydrophobic and the hydrophilic blocks. A suitable functional group may be provided from one or more monomers selected from the group consisting of 2-aminoethyl methacrylate hydrochloride, N-(3-aminopropyl)methacrylamide hydrochloride) or similar monomer with primary amino group or the group, which is convertible to the amino group. In addition, any of the homologues thereof may also be used. In the preferred embodiment the monomer is 2-aminoethyl methacrylate hydrochloride.

Figure 1C:
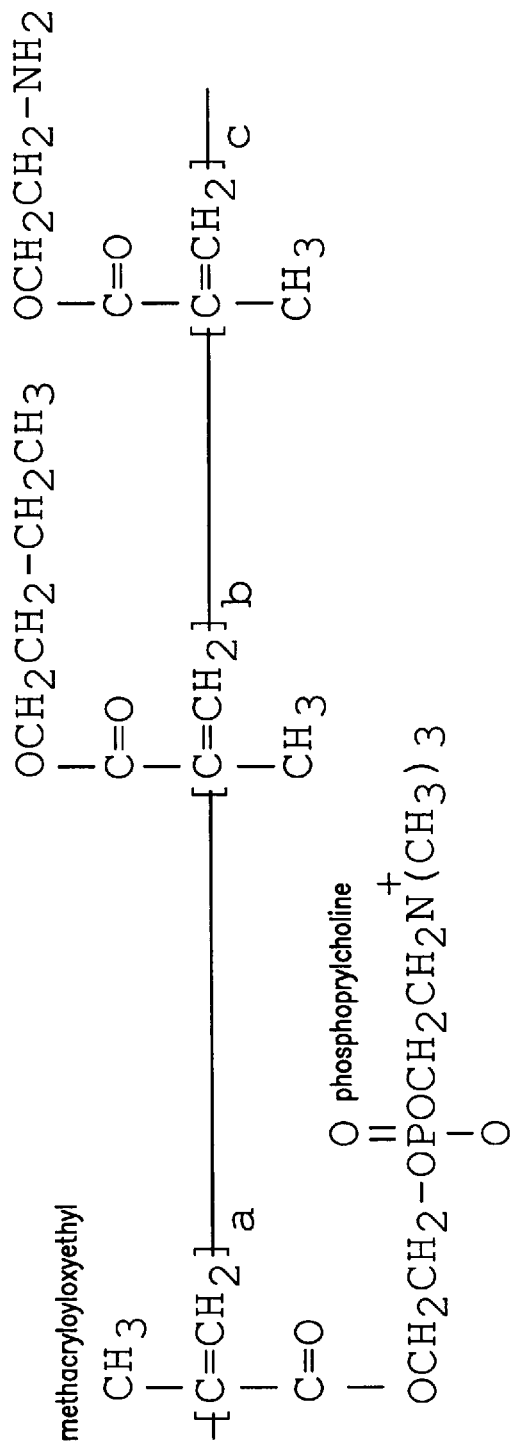
FIG. 1C illustrates the structure of a copolymer coating synthesized using methacrylate monomers with a functional group for the subsequent attachment of a biomolecule according to the present invention.

FIG. 1C illustrates the structure of a copolymer coating synthesized using methacrylate monomers with a functional group for the subsequent attachment of a biomolecule according to the present invention. As seen in this illustrated example, the hydrophobic group is provided through a butyl group, the hydrophilic group is provided by MPC while the functional group is provided by an aminoethyl group.

Figure 2:
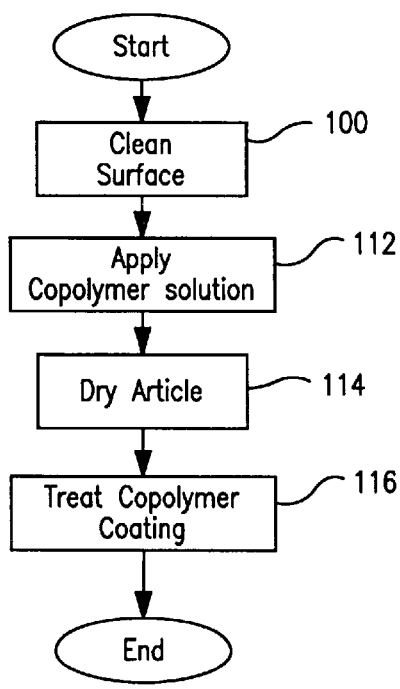
FIG. 2 depicts the basic steps for providing a medical article with the biocompatible coating of the present invention.

FIG. 2 depicts the basic steps for providing a medical article with the biocompatible coating of the present invention. First at step 100 the surface of the article is cleaned. This may be accomplished in any acceptable manner according to the specific material from which the article is constructed. For a silicone article, for example, the surface is cleaned by supercritical fluid extraction, while for a polyurethane article the surface is cleaned with ethanol. Next at step 112 an organic solvent-based solution of the copolymer coating synthesized using methacrylate or acrylate monomers with a functional group (primary amino group) for subsequent attachment of the biomolecule is applied. Specific details concerning the creation of the copolymer coating are discussed below with regard to FIG. 3. The article is then dried at step 114, driving off the organic solvent and leaving a coating of copolymer. Once such a coating is present, the copolymer coating is further treated at step 116 so as to achieve a desired level of biocompatibility. In the preferred embodiment this is accomplished by coupling heparin to the coating. Specific details concerning the coupling of heparin are discussed below with regard to FIG. 3

Figure 3:
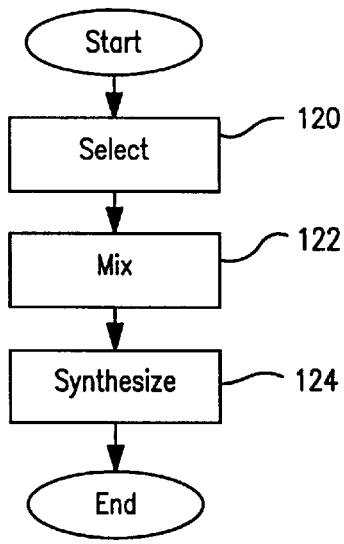
FIG. 3 depicts the steps used to create an acceptable copolymer coating used in the present invention.

FIG. 3 depicts the steps used to create an acceptable copolymer coating used in the present invention. First at step 120 an acceptable mixture of hydrophobic monomer/ hydrophilic monomer/functional monomer is created. As discussed above, the monomers are selected in order to optimize the solubility of the copolymer in an organic solvent (preferably ethanol), its insolubility in water (before and after heparin coupling), the heparin coupling efficacy and heparin bioactivity. In the preferred embodiment the copolymer coating is synthesized using methacrylate or acrylate monomers with a functional group (primary amino group) for subsequent attachment of heparin. An acceptable copolymer coating may be formed by selecting the monomers n-butyl methacrylate (BMA); 2-methacryloyloxyethyl phosphorylcholine (MPC); and 2-aminoethyl methacrylate in the relative molar proportions of 65:20:15. The selected monomers are mixed together at step 122 and the polymer is synthesized at step 124 by conventional free radical polymerization. An acceptable synthesis conditions are typically using ethanol at 60° Celsius for 24 hours. Synthesis results in a copolymer coating which is soluble in alcohol, insoluble in water and to which heparin may be readily coupled. Thereafter the copolymer is ready for application to the medical article.

Figure 4:
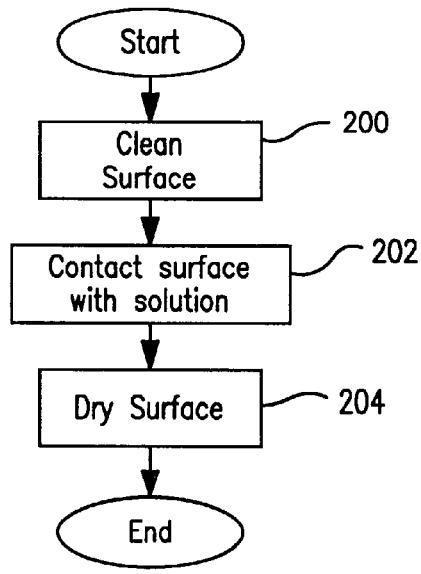
FIG. 4 depicts the steps used to coat the surface of a medical article with the copolymer coating of the present invention.

FIG. 4 depicts the steps used to coat the surface of a medical article with the copolymer coating of the present invention. After preliminary cleaning of the surface of medical article at 200, alcohol solution of the polymer contacts the surface by either pumping of the solution through the device or immersing the device into the solution at 202. The time, during which surface is in contact with solvent should be in the range from several seconds to several minutes. The surface of the medical article is then dried at 204 (i.e., removing the alcohol carrier). This can be done by a variety of methods. Preferably, they are carried out in one step by flushing the surface of the substrate with moist air (e.g., greater than 50% relative humidity).

Figure 5:
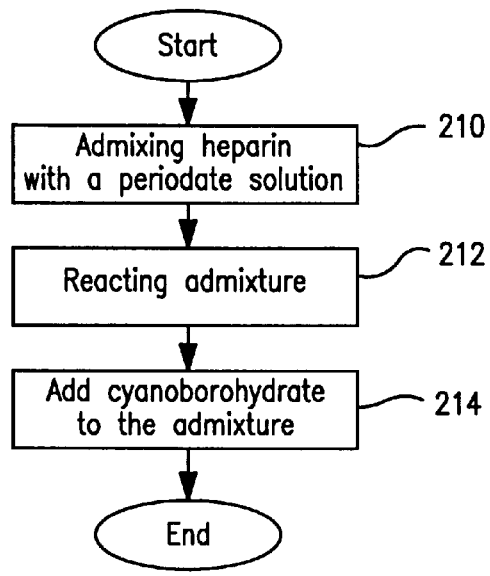
FIG. 5 depicts the steps used to couple a biomolecule to the copolymer coating.

FIG. 5 depicts the steps used to couple a biomolecule to the copolymer coating. One particularly preferred method is to couple heparin using an oxidation method involving the use of periodate. The basic steps of the preparation of such a solution are shown. These steps consist of admixing heparin with a periodate solution shown as 210; reacting the admixture shown as 212; and adding cyanoborohydrate to the admixture at 214. Essentially, the prepared heparin solution used to couple heparin to the copolymer coating is described in Verhoeven et al. U.S. Pat. No. 5,679,659 Method For Making Heparinized Biomaterials assigned to the assignee of the present invention and incorporated herein by reference. The heparin, is contacted with a periodate in a buffered aqueous solution and allowed to react. This controlled oxidation provides a limited number of reactive aldehyde groups per molecule. The periodate is a water-soluble periodate, preferably, an alkali metal periodate, such as sodium periodate. When the biomolecule is heparin, the amount of periodate used is sufficient to react with no more than two of the sugar units in the heparin molecule (i.e., the basic disaccharide residues constituting the structure of the glycosaminoglycan). If the periodate used is sodium periodate and the heparin used is a commercially available injectable form of heparin (e.g., its sodium salt with activity of 160 units/milligram), the weight ratio of heparin to periodate should be about 30:1 or less in order to react with no more than two of the sugar units in the heparin molecule. It will be appreciated by those skilled in the art that the amount of periodate required for other periodate compounds and other forms of heparin can be determined by conventional calculation and empirical tests.

The reaction between heparin and periodate takes place in an aqueous buffer solution. Generally, buffers having a pH in a neutral to slightly acidic range of about 4.5 to about 8 can be used. A lower pH (e.g., an acetate buffer at pH 4.5) is preferred if a rapid reaction is desired while a more neutral pH (e.g., a phosphate buffer at pH 6.88) is preferred for a slower reaction with a longer storage life. With the acetate buffer at a pH of 4.5, the reaction should proceed for about 3 hours, while with a phosphate buffer at a pH or 6.88, the reaction should proceed for about 16 hours. If desired, the reacted mixture may then be stored prior to use at about 5° C.

The reacted mixture is diluted and the pH adjusted in order to bring the pH of the mixture to a pH that is favorable for the coupling reaction between the biomolecule and the copolymer coating synthesized using methacrylate or acrylate monomers with a functional group (primary amino group). A mild reducing agent, such as sodium cyanoborohydride, is added to the diluted mixture to effect the reduction of the bonds formed between the reactive aldehyde groups on the oxidized biomolecule and the amine functional groups on the copolymer coated on the substrate surface. The substrate surface being treated is then contacted with (e.g., immersed in or flushed with) the diluted mixture at a sufficient temperature and for a sufficient time to complete the reaction (i.e., attach the biomolecule). This time can range from about 30 seconds to about 2 hours at temperatures ranging from about 20° C. to about 60° C.

Once the heparin solution is prepared it is used to couple heparin to the medical article. In particular, the heparin solution is brought into contact with the MPC copolymer coated surface of the medical article. For example, the 2000 ml of the heparin solution prepared according to the above is carefully dispensed in a reactor glass chamber. The temperature of the water circulation bath is set at 50° C., while same pumping speed is maintained. Next, The reactor chamber is filled in such a way that desired article may be immersed in the heparin solution. Stirring is started so as to prevent that a strong vortex is formed. The immersion of the medical article in the heparin solution is allowed to continue for 120 minutes at 50° C. Next, the article is dried in the way described above.

Figure 6:
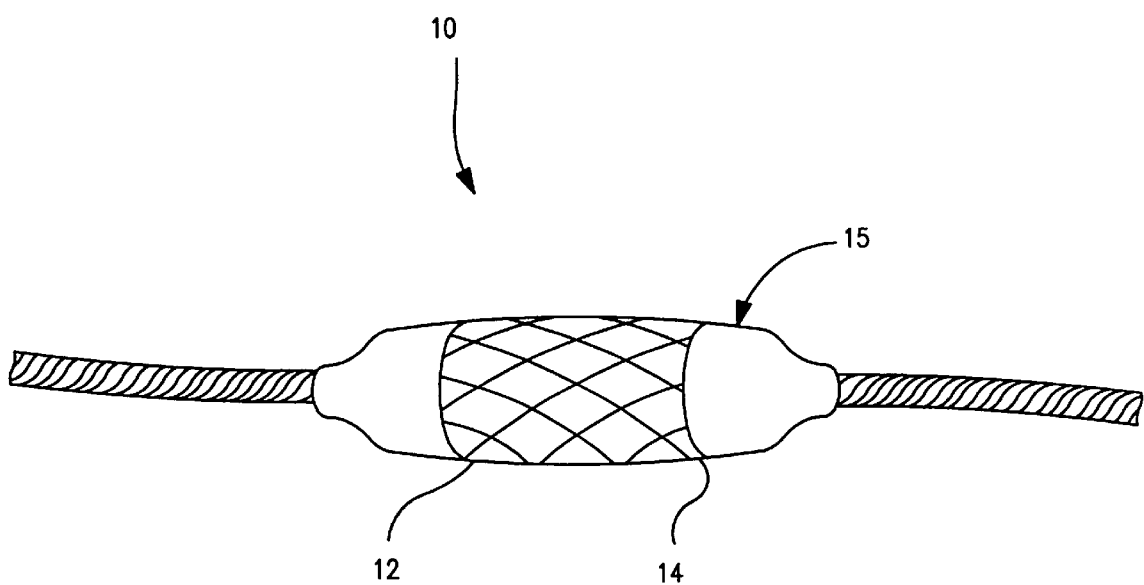
FIG. 6 is an illustration of a stent (shown around a balloon) treated with the copolymer coating synthesized using methacrylate or acrylate monomers with a functional group (primary amino group) for subsequent attachment of the biomolecule according to the present invention.

The method of the present invention is particularly applicable to stents. The term "stent" refers to any device capable of being delivered by catheter. FIG. 6 is an illustration of a stent 10 (shown around a balloon 15) treated with the copolymer coating synthesized using methacrylate or acrylate monomers with a functional group (primary amino group) for subsequent attachment of the biomolecule according to the present invention. Stent 10 includes lumen wall-contacting surface 12 and lumen-exposed surface (not shown). Where the stent is shaped generally as a tube-like structure, including a discontinuous tube or ring-like structure, the lumen-wall contacting surface is the outside surface of the tube and the lumen-exposed surface is the inner surface of the tube. When in place, the outer surface is in contact with a portion of a wall of a lumen, and the inner surface is in contact with blood. Stent 10 is coated with the copolymer coating synthesized using methacrylate or acrylate monomers with a functional group (primary amino group) with a biomolecule, thus forming blood compatible surface 14. Typically, both the lumen wall-contacting surface 12 and the lumen-exposed surface are coated with the copolymer coating synthesized using methacrylate or acrylate monomers with a functional group (primary amino group) and biomolecule, although, depending on the materials used to make the stent, only the lumen-exposed surface would need to be. Balloon 15 is positioned adjacent the lumen-exposed surface of the stent to facilitate delivery of the stent.

Other suitable stents include a deformable metal wire stent useful as a stent framework, such as that described in U.S. Pat. No. 4,886,062 (Wiktor), which discloses preferred methods for making a wire stent. Other useful metallic stents include those of U.S. Pat. No. 4,733,665 (Palmaz) and U.S. Pat. No. 4,800,882 (Gianturco). Other suitable stents include the Palmaz-Schatz coronary stent (Johnson & Johnson Interventional, Warren, N.J.) and stents from memory-shaped metals such as self-expanding nitinol stents including that available under the trade designation CARDIO-COIL from Medtronic, Eden Prairie, Minn., and disclosed in U.S. Pat. No. 5,372,600. Preferred stents for use in this invention should be flexible to navigate lumens during insertion, biocompatible, and reliably expand and embed in the lumen wall.

The method of the present invention also is particularly applicable to blood gas exchange devices, e.g., oxygenators. This includes both sheet and hollow fiber (or tubular) forms of membrane oxygenators, which are well known in the art. Hollow fibers suitable for use with oxygenators are made blood compatible, typically by exposing the hollow fibers to the alcohol solution of the copolymer synthesized using methacrylate or acrylate monomers with a functional group (primary amino group) for subsequent attachment of the biomolecule; drying with moist air to remove solvent and excess compound; and then exposing it to an aqueous biomolecule solution for a time sufficient to couple the biomolecule to the polymer and to form blood compatible hollow fibers.

Figure 7:
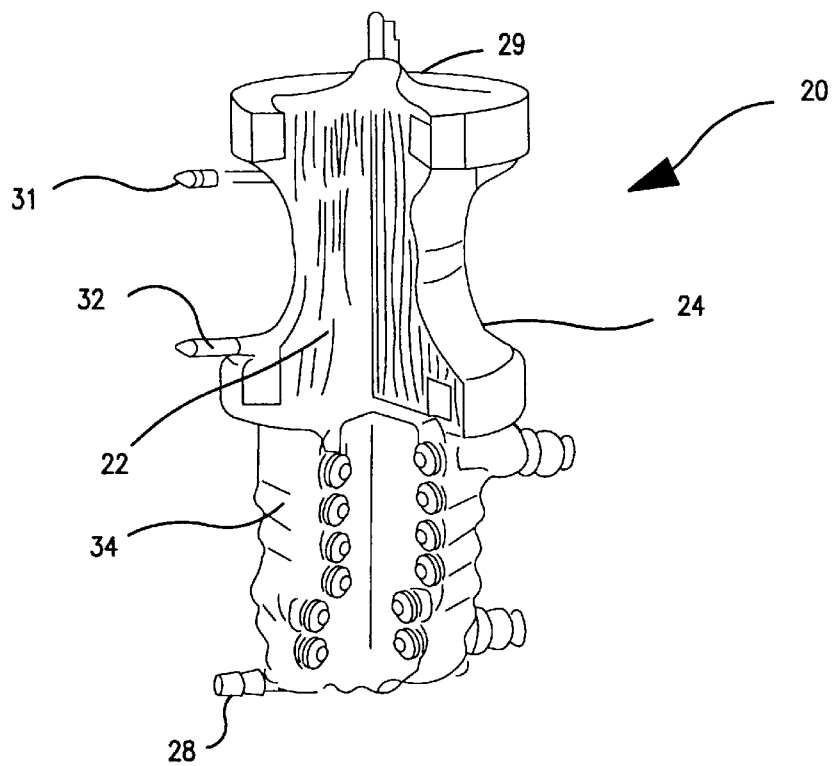
FIG. 7 illustrates a simplified diagram of a blood oxygenator wherein a plurality of hollow fibers is disposed within hollow housing.
Figure 8:
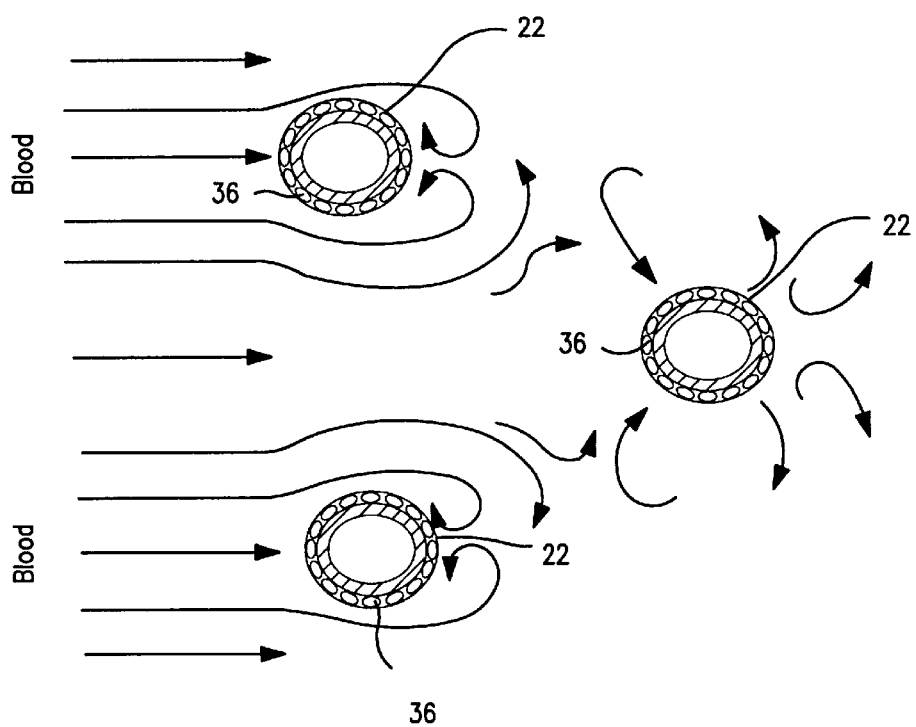
FIG. 8 illustrates blood flow through a plurality of hollow fibers coated with the present invention is disposed within hollow housing.

FIG. 7 illustrates a simplified diagram of a blood oxygenator 20, wherein a plurality of hollow fibers 22 is disposed within hollow housing 24. Though depicted in a linear arrangement, it is to be understood that the fibers could be arranged in a variety of configurations, including a circular or spiral arrangement, as well as being wrapped around a core or the like. The fibers are supported within housing 24 by end walls 25 and 26. Blood flow inlet 28 permits the passage of blood through fibers 22, as depicted in FIG. 8, and thereafter out through blood flow outlet 29. Although these FIGS. depict blood flow through the fibers, it is to be understood that, depending upon the desired characteristics of the oxygenator, blood can flow either through or over the hollow fibers. Gas (e.g., oxygen) flows into housing 24 via gas inlet port 31. The gas flows over the fibers and out of housing 24 via gas outlet port 32. The hollow fibers 22 and other surface of the oxygenator would be made blood compatible by exposing the entire surface of the fibers to the copolymer coating synthesized using methacrylate or acrylate monomers with a functional group (primary amino group); drying to remove solvent and excess compound; and then exposing it to a biomolecule for a time sufficient to couple the biomolecule to the silicon and form a biocompatible membrane, as represented by layer 36 in this FIG. 8.

Although the examples described below involve treatment on polymeric films or tissue culture plates as the substrate surfaces, it is not intended that this invention be so limited.

EXPERIMENTAL EXAMPLES
Synthesis of MPC-BMA-AEMA Copolymer

The MPC, BMA and AEMA monomers in the proportion 20:65:15, respectively, were dissolved into ethanol (analytical grade) to the total solids concentration of 1 mole/L. Glass ampoules (100 ml) were filled with monomers solution and 2,2'-azobisisobutyronitrile (AIBN) was dissolved to a concentration of 1 mmole/L at room temperature. Argon gas was bubbled through the solution to displace the oxygen, and then the ampoule was sealed. The polymerization was carried out at 60° C. for 1 hour. After cooling to the temperature of 30° C. or lower, the content of the ampoule was poured into 2 L of the mixture of diethyl ether and N,N-dimethylformamide (DMF) (9:1 by volume) to remove unreacted monomer and to precipitate the copolymer formed. The precipitated copolymer was filtered off with the glass filter (pores size of 5 $\mu$m) and dried in vacuo. The dry copolymer was kept in refrigerator at 4° C. until use.

Thereafter to apply the copolymer to the surface of medical article, the copolymer is dissolved in ethanol to the concentrations from 0.1 wt % to 5 wt %, preferably 1.0% and this solution is ready for application to the medical article.

Application to the Medical Article

Copolymer solution is pumped through the Medtronic PVC, PU tubing, Maxima hollow fibers oxygenators for one minute and then the tubing is dried by blow of the air through the tubing for 1 h. Medtronic Wiktor stents and Medtronic DLP's PVC cannulae are dip coated at the lifting speed from 10 cm to 100 cm per minute. The coated devices are dried at room temperature for 12 h in air.

Immobilization of a Biomolecule

The heparin, is contacted with a periodate in a buffered aqueous solution and allowed to react. If the periodate used is sodium periodate and the heparin used is a commercially available injectable form of heparin (e.g., its sodium salt with activity of 160 units/milligram), the weight ratio of heparin to periodate should be about 30:1 or less in order to react with no more than two of the sugar units in the heparin molecule. The reaction between heparin and periodate takes place in an aqueous buffer solution. With the acetate buffer at a pH of 4.5, the reaction should proceed for about 3 hours. The reacted mixture is diluted and the pH adjusted in order to bring the pH of the mixture to a pH=9 that is favorable for the coupling reaction between the biomolecule and the copolymer coating synthesized using methacrylate or acrylate monomers with a functional group (primary amino group). A mild reducing agent, such as sodium cyanoborohydride, is added to the diluted mixture to effect the reduction of the bonds formed between the reactive aldehyde groups on the oxidized biomolecule and the amine functional groups on the copolymer coated on the substrate surface. This time is about 2 hours at temperature of about 60° C.

Blood Testing

We have performed two types of tests aiming at the determination of blood activation and have observed the similar tendency in both experiment: A surface coated with the present invention, that is a surface having a copolymer coating synthesized using methacrylate or acrylate monomers with a functional group a biomolecule attached thereto provided a superior blood compatible surface as compared to any of the other surfaces tested. These other surfaces included both uncoated polymers as well as polymers coated with MPC, but without the attachment of a biomolecule, as taught by the present invention.

TABLE 1

Clotting time test using recalcified human Plasma Rich Protein (PRP).

| Material | Clotting time, sec |
|---|---|
| Polypropylene (PP) | 595 ± 38 |
| PP-(MPC-DMA) | 619 ± 25 |

TABLE 1-continued

Clotting time test using recalcified human Plasma Rich Protein (PRP).

| Material | Clotting time, sec |
|---|---|
| Polyurethane (PU) | 592 ± 12 |
| PU-(MPC-BMA) | 623 ± 9 |
| PU-(MPC-BMA-PMBU) | 636 ± 8 |
| PU-(MPC-BMA-Heparin) | 1350 ± 30 |

"PMBU" stands for Polymethoxyacryloyloxyethyl butylurethane
"DMA" stands for dodecyl methacrylate.

Table 1 shows the results for several surfaces of a clotting time test using recalcified human PRP performed in accordance with the teachings of "Platelet Procoagulant Surface As An Essential Parameters For The In Vitro Evaluation Of The Blood Compatibility Of Polymers," J. Mater.Sci.Mater.Med.6, 367 (1995). In particular six surfaces where tested including both uncoated polymers as well as polymers coated with MPC, but without the attachment of a biomolecule, as taught by the present invention. The six surfaces treated were: Polypropylene (PP);PP-(MPC-DMA); Polyurethane (PU); PU-(MPC-BMA), PU-(MPC-BMA-PMBU) and PU-(MPC-BMA-Heparin.) As shown in Table 1 the MPC copolymers without heparin attachment did not increase the clotting time of PP and PU. Attachment of heparin resulted in a two-fold increase of the clotting time and, therefore, MPC-Heparin combination is superior to any other MPC copolymers in terms of preventing thrombin generation in blood. Data, shown in Table 2 also supports this conclusion.

TABLE 2

Ratios of blood activation parameters (coated/non-coated) from loop studies. Flow condition:pulsatile flow (pulse frequency = 1Hz; Average shear rate at surface = 133 s$^{-1}$). Human blood was heparinized (0.6–0.8 IU/ml).

| Material | βTG | TAT |
|---|---|---|
| PU—(MPC—PMB—PMBU)/PU | 0.56 ± 0.41 | 0.80 ± 0.38 |
| PP—(MPC—DMA)/PP | 1.1 ± 0.56 | 2.0 ± 2.7 |
| PU—(MPC—PBM-Heparin)/PU | 0.58 ± 0.36 | 0.39 ± 0.11 |
| PP—(MPC—PBM-Heparin)/PP | 0.15 ± 0.09 | 0.27 ± 0.09 |

Table 2 shows the ratios of blood activation parameters (coated/non-coated from the loop studies. The loop studies were performed with pulsatile flow (pulse frequency=1 Hz; Average shear rate at surface=133 s$^{-1}$). Human blood was heparinized (0.6–0.8 IU/ml). Thrombin-antithrombin complex (TAT) is a marker of thrombin generation. The higher is its concentration in blood, the higher is activation of coagulation system. Clearly, the was no statistically significant difference in terms of TAT concentration upon coating of PU and PP with MPC copolymers, unless the heparin was coupled to such copolymers. βTG is a marker of platelet activation. Although MPC copolymers did reduced platelet adhesion and activation, the coupling of heparin to MPC coating on PP resulted in the further reduction of platelet activation, as shown in this table.

Results

The surface featuring a copolymer coating synthesized using methacrylate or acrylate monomers with a functional group (primary amino group) and to which a biomolecule is attached clearly improves the hemocompatibility and reduces the propensity to inflammation of the surface, as compared to both untreated surfaces and surface coated with the monomer 2-methacryloyloxyethyl phosphorylcholine (MPC,) only.

Figure 9:
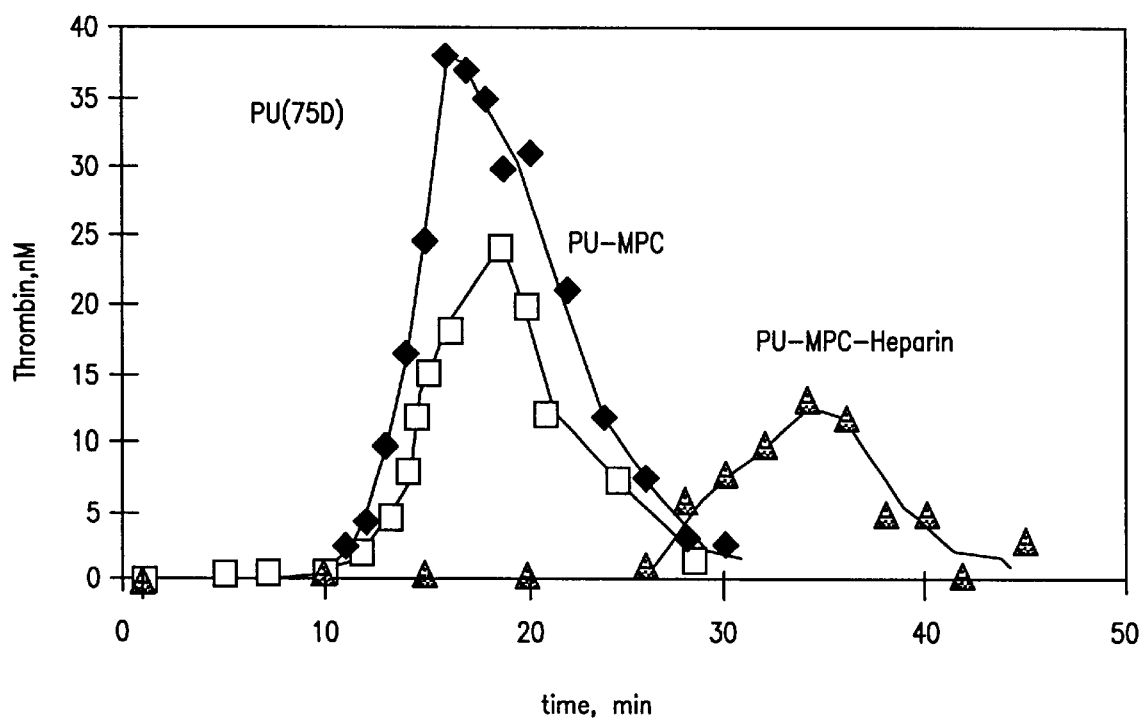
FIG. 9 depicts the relative difference between the present invention and materials not featuring the present invention in reference to thrombin generation.

The relative superiority of the present invention compared to uncoated surfaces and surface coated only with MPC may be further seen in FIG. 9. FIG. 9 depicts the relative difference between the present invention and materials not featuring the present invention in reference to thrombin generation. In particular, three thrombin generation curves from recalcified platelet rich plasma are shown. The three curves correspond with three separate materials, the first designated PU being an untreated 75D-type polyurethane (a suitable 75D polyurethane is available as PELLETHANE 75D from Dow Chemical Corp.), the second curve designated PU-MPC being a 75D polyurethane surface treated using an MPC-type coating, the MPC-type coating provided by the above-described process of providing a copolymer coating synthesized using methylacrylate or acrylate monomers with a functional group, but without the functional group being heparinized. Finally, the third curve depicts the polyurethane surface treated with a copolymer coating as described above and in which the functional group has had heparin coupled thereto. As seen, thrombin generation occurs quickest and in the greatest relative amount for the untreated polyurethane surface while the PU-MDC heparinized surface, according to the present invention, exhibits the least amount of thrombin generation in the greatest relative time. This is an important and crucial difference in that, from a patient's perspective, much less thrombin in the blood stream is generated overall using the present invention as compared to prior surfaces. In particular regards to a PU-MPC surface without heparinization, the present invention is almost half as thrombogenic while requiring much greater time.

Although as discussed above ethanol is the preferred solvent for the copolymer solution according to the present invention, it should be understood other organic solvents may also be used, including isopropyl alcohol, acetone, butanone, hexane, n-octane, isooctane, cyclohexane, benzene, toluene, methyl, ethyl, and isopropyl formate, methyl, ethyl, and isopropyl acetate, methyl, ethyl, and isopropyl propionate, and ethyl acetate. What is most important is that the organic solvent selected is such that it will permit the selected monomers to readily dissolve but not the polymer or polymeric substrate to which the copolymer solution is coated. Moreover, as used herein "polymer" or "polymeric surface" generally may include polymeric materials such as silastic or other silicone-based materials, polyethylene tecephtalate (PET), dacron, knitted dacron, velour dacron, polyglacin, chromic gut, nylon, silk, bovine arterial graft, polyethylene (PE), polyurethane (PU), PMMA [poly-(methyl methacrylate), latex, poly vinyl] alcohol (PVA), poly (hydroxyethyl methacrylate (PHEMA), poly (glycolic acid), poly (acrylonitrile) (PAN), floroethylene-co-hexafluoropropylene (FEP), polypropylene (PP), polyvinylchloride (PVC), and polyvinylidenefluoride (PVDF), and teflon (PTFE). Medical articles made using these materials can be coated or uncoated, and derivatized or underivatized, prior to being coated with the copolymer coating synthesized using methacrylate or acrylate monomers with a functional group (primary amino group).

As used herein a "medical article" is defined as any article or device that has surfaces that contact tissue, blood, or other bodily fluids in the course of their operation, which fluids are subsequently used in patients. This can include, for example, extracorporeal devices for use in surgery such as blood oxygenators, blood pumps, blood sensors, tubing used to carry blood and the like which contact blood which is then returned to the patient. This can also include endoprostheses implanted in blood contact in a human or animal body such as vascular grafts, stents, pacemaker leads, heart valves, and the like that are implanted in blood vessels or in the heart. This can also include devices for temporary intravascular use such as catheters, guide wires, and the like which are placed into the blood vessels or the heart for purposes of monitoring or repair.

A "biomolecule" is defined as a biologically active molecule. As used herein this term includes, for example: antibacterial and antimicrobial agents; anticoagulant and antithrombotic agents; platelet agents; anti-inflammatories; enzymes; catalysts; hormones; growth factors; drugs; vitamins; antibodies; antigens; nucleic acids; dyes (which act as biological ligands); DNA and RNA segments; and proteins and peptides. The biomolecules can be synthetically derived or naturally occurring. These biomolecules include heparin, prostaglandin $E_1$ (PGE1), ticlopidine, plasmin, urokinase, TPA, polyethylene oxide (PEO), and FUT-175. Heparin inhibits the coagulation of blood by interacting with antithrombin III and thrombin to inhibit the conversion of fibrinogen to fibrin. Ticlopidine and prostaglandin $E_1$ inhibit the activation of platelets. Plasmin, urokinase, and TPA are serin proteases which lyse protein deposits and networks. Polyethylene oxide minimizes protein adsorption, and FUT-175 inhibits the formation of thrombin.

A "biocompatible" material is one that does not generally cause significant adverse reactions (e.g., toxic or antigenic responses) in the body, whether it degrades within the body, remains for extended periods of time, or is excreted whole. Ideally, a biocompatible material will not induce undesirable reactions in the body as a result of contact with bodily fluids or tissue, such as tissue death, tumor formation, allergic reaction, foreign body reaction (rejection) or inflammatory reaction.

A "blood compatible" material is one that will not induce undesirable reactions in the body as a result of contact with blood, such as blood clotting. This can be demonstrated by reduced thrombin generation, for example.

It will be appreciated by those skilled in the art that while the invention has been described above in connection with particular embodiments and examples, the invention is not necessarily so limited and that numerous other embodiments, examples, uses, modifications and departures from the embodiments, examples and uses are intended to be encompassed by the claims attached hereto. The entire disclosure of each patent and publication cited herein is incorporated by reference, as if each were individually incorporated by reference.

We claim:

1. A method of coating a biocompatible medical article having a polymeric surface, comprising:

providing the medical article;

cleaning the polymeric surface;

synthesizing, in an organic solvent and apart from the medical article, a mixture comprising a first hydrophobic monomer selected from the group consisting of hydrophobic methacrylate monomers and hydrophobic acrylate monomers, a second functional monomer having pendant chemically reactive amine groups capable of forming co-valent bonds with biologically active compounds, and a third hydrophillic monomer, the synthesis yielding a copolymer solution;

coating the polymeric surface of the medical article with the copolymer solution to produce a coated copolymeric surface; and coupling a biomolecule onto the coated surface through the ordered steps of: (a) admixing heparin with a periodate solution to produce an admixture, (b) reacting the admixture and adding cyanoborohydride thereto produce a reacted admixture, (c) diluting the reacted admixture to form a diluted reacted admixture, and (d) treating the coated copolymeric surface with the diluted reacted admixture to render the resulting treated and coated polymeric surface amphiphobic.

2. The method of claim 1 wherein the first monomer, second monomer and third monomer are mixed together in the relative molar proportions of 65:15:20 respectively.

3. The method of claim 1 wherein the biomolecule is heparin.

4. The method of claim 1 wherein the first monomer is selected from the group consisting of butyl methacrylate, butyl acrylate, dodecyl methacrylate, dodecyl acrylate, heptyl acrylate, hexadecyl methacrylate, and octyl methacrylate.

5. The method of claim 1 wherein the first monomer is butyl methacrylate.

6. The method of claim 1 wherein the second monomer is 2-aminoethyl methacrylate hydrochloride N-(3-aminopropyl)methacrylamide hydrochloride).

7. The method of claim 1 wherein the second monomer is 2-aminoethyl methacrylate hydrochloride.

8. The method of claim 1 wherein the first monomer is selected from the group consisting of acrylic or methacrylic monomers, which have a primary amino group.

9. The method of claim 1 wherein the third monomer is selected from the group consisting of methacryloyl oxyethyl phosphorylcholine, acrylamide, poly(ethylene glycol) methacrylate, hydroxyethyl methacrylate, hydroxypropyl methacrylate, acrylic acid, methacrylic acid, 2,3-dihydroxypropyl acrylate, 2,3-dihydroxypropyl methacrylate, 3-sulfopropyl methacrylate, methacrylamidopropyltrimethylammonium chloride.

10. The method of claim 1 wherein the third monomer is methacryloyl oxyethyl phosphorylcholine.

11. The method of claim 1 wherein the first monomer is selected from the group consisting of acrylic or methacrylic monomers which have a hydrophilic moiety, which makes the monomer soluble in water and the copolymer formed therefrom wettable.

\* \* \* \* \*

UNITED STATES PATENT AND TRADEMARK OFFICE
CERTIFICATE OF CORRECTION

PATENT NO. : 6,258,371 B1
DATED : July 10, 2001
INVENTOR(S) : Edouard Koulik et al.

It is certified that error appears in the above-identified patent and that said Letters Patent is hereby corrected as shown below:

<u>Title page,</u>
Item [75], Inventors, replace "Larik Vincent" with -- Vincent Larik --.

Signed and Sealed this

Twenty-sixth Day of March, 2002

*Attest:*

*Attesting Officer*

JAMES E. ROGAN
*Director of the United States Patent and Trademark Office*